US011504716B2

(12) United States Patent
Ferguson et al.

(10) Patent No.: US 11,504,716 B2
(45) Date of Patent: Nov. 22, 2022

(54) MULTIWELL DEVICE AND METHOD OF USE

(71) Applicant: Pall Corporation, Port Washington, NY (US)

(72) Inventors: James George Ferguson, Chichester (GB); Jeffrey Toma, Ann Arbor, MI (US); William Scott Gordon, Whitmore Lake, MI (US); Bharath Kumar Raghavan, Merrimack, NH (US); Daniel Dalessio, Walpole, MA (US)

(73) Assignee: Pall Corporation, Port Washington, NY (US)

( * ) Notice: Subject to any disclaimer, the term of this patent is extended or adjusted under 35 U.S.C. 154(b) by 314 days.

(21) Appl. No.: 16/893,593

(22) Filed: Jun. 5, 2020

(65) Prior Publication Data

US 2021/0379583 A1    Dec. 9, 2021

(51) Int. Cl.
*B01L 3/00* (2006.01)
*B01D 61/18* (2006.01)
*C07K 1/34* (2006.01)

(52) U.S. Cl.
CPC ............ *B01L 3/5085* (2013.01); *B01D 61/18* (2013.01); *C07K 1/34* (2013.01); *B01L 2300/0681* (2013.01); *B01L 2300/0829* (2013.01); *B01L 2300/0851* (2013.01); *B01L 2300/0858* (2013.01)

(58) Field of Classification Search
None
See application file for complete search history.

(56) References Cited

U.S. PATENT DOCUMENTS

| | | | |
|---|---|---|---|
| 6,391,241 B1 | 5/2002 | Cote et al. | |
| 7,135,117 B2 | 11/2006 | Kane et al. | |
| 7,618,592 B2 | 11/2009 | Burnham et al. | |
| 7,658,886 B2 | 2/2010 | Olivier et al. | |
| 8,007,743 B2 | 8/2011 | Clark et al. | |
| 8,753,588 B2 | 6/2014 | Desilets et al. | |
| 9,427,512 B2 | 8/2016 | DelGiacco et al. | |
| 10,669,327 B2 | 6/2020 | Quinones-Garcia et al. | |
| 2002/0104795 A1* | 8/2002 | Cote | B01L 3/5025 264/153 |
| 2005/0095175 A1 | 5/2005 | Desilets et al. | |
| 2011/0301342 A1 | 12/2011 | Wang et al. | |

FOREIGN PATENT DOCUMENTS

| | | |
|---|---|---|
| CN | 109046026 A | 12/2018 |
| EP | 0359249 A2 | 3/1990 |
| EP | 1 524 033 A1 | 4/2005 |
| JP | 2002-511931 A | 4/2002 |

(Continued)

OTHER PUBLICATIONS

China National Intellectual Property Administration, Office Action issued in counterpart Chinese Patent Application No. 202110612509.1, dated Jun. 16, 2022.

(Continued)

*Primary Examiner* — J. Christopher Ball
(74) *Attorney, Agent, or Firm* — Leydig Voit & Mayer, Ltd.

(57) ABSTRACT

Multiwell devices and methods of filtration using the multiwell devices are disclosed.

5 Claims, 13 Drawing Sheets

(56) References Cited

FOREIGN PATENT DOCUMENTS

Figure 1A:
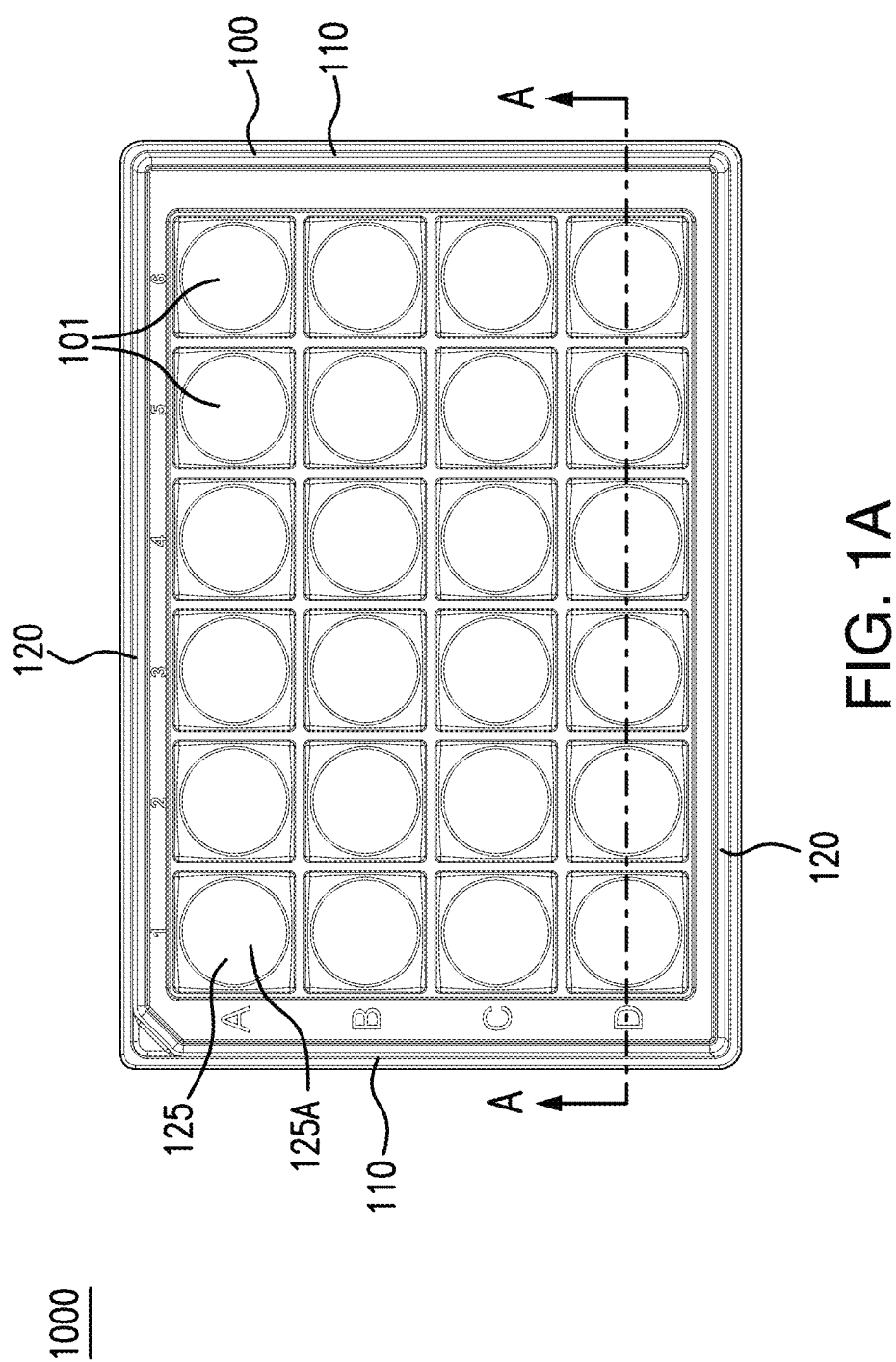

| | | |
|---|---|---|
| JP | 2005-152887 A | 6/2005 |
| JP | 2013-531623 A | 8/2013 |
| JP | 2019-511498 A | 4/2019 |
| KR | 10-2013-0138126 A | 12/2013 |

OTHER PUBLICATIONS

"Isolute Filter+ High Performance Filtration Plates" (2017), pp. 1-4, retrieved from the Internet on Jun. 2, 2022, URL: https:/lcms.labrulez.com/paper/16849.

Japanese Patent Office, Office Action issued in counterpart Japanese Patent Application No. 2021-081673, dated Jun. 14, 2022.

Prashad et al., "Depth filtration: Cell clarification of bioreactor offloads", *Filtration & Separation*, vol. 43, Issue 7, pp. 28-30 (2006).

European Patent Office, extended European Search Report in counterpart European Patent Application No. 21 174 901.5, dated Oct. 29, 2021.

\* cited by examiner

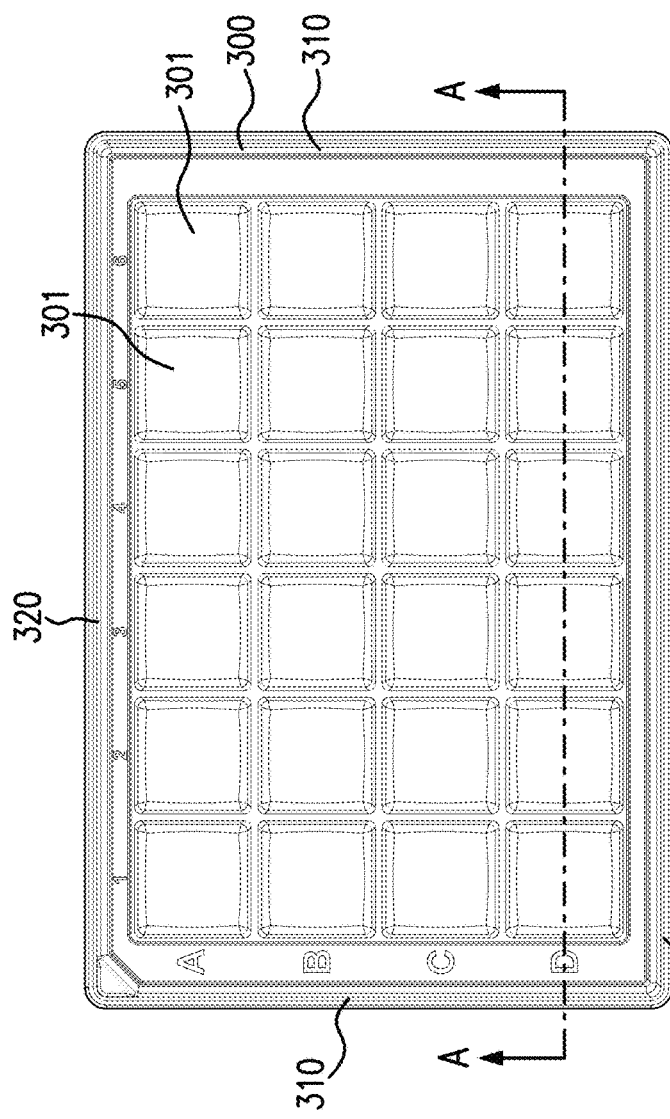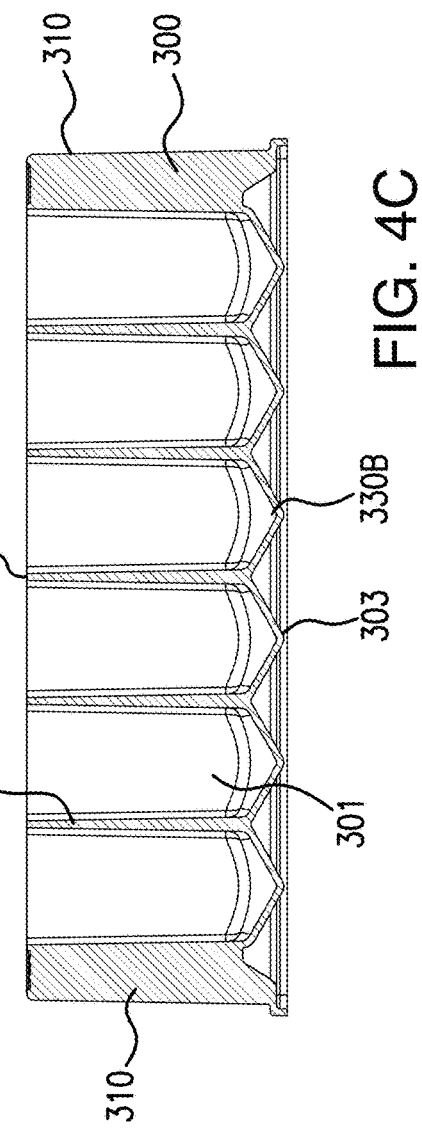

MULTIWELL DEVICE AND METHOD OF USE

BACKGROUND OF THE INVENTION

After growing cells, some procedures for obtaining proteins of interest include centrifuging cell samples in centrifuge tubes, aspirating off the supernatant, and using a syringe filter to separate the proteins from the other material in the remaining fluid.

There is a need for improved devices and methods for obtaining proteins of interest.

The present invention provides for ameliorating at least some of the disadvantages of the prior art. These and other advantages of the present invention will be apparent from the description as set forth below.

BRIEF SUMMARY OF THE INVENTION

An embodiment of the invention provides a multiwell device for processing fluid samples comprising: an upper receiving plate, a middle filtration plate, and a lower collection plate; (a) the upper receiving plate comprising a plurality of wells for receiving fluid samples comprising cells, the plurality of wells in the upper receiving plate each including a side wall having an inner surface, a bottom end including a downwardly projecting collar and a bottom fluid flow port, wherein the upper receiving plate includes two pairs of opposing sidewalls, and each opposing sidewall in at least one of the two pairs of opposing sidewalls in the upper receiving plate includes a groove having a lower opening for receiving side walls of corresponding wells at corresponding side walls on the middle filtration plate; (b) the middle filtration plate comprising a plurality of wells, the plurality of wells in the middle filtration plate each comprising a filter for filtering the fluid sample passing through the bottom fluid flow port of a corresponding well in the upper receiving plate; each filter comprising an upper depth filter layer having an average pore size in the range of from about 1 micrometer to about 20 micrometers, an upstream surface and an downstream surface, the upstream surface of the depth filter layer providing the upstream surface of the filter; a middle layer comprising a microporous membrane having an average pore size in the range of from about 0.4 micrometers to about 0.8 micrometers; and a bottom layer having an upstream surface and a downstream surface, comprising a microporous membrane having an average pore size of about 0.2 micrometers, the downstream surface of the microporous membrane having an average pore size of about 0.2 micrometers providing the downstream surface of the filter; wherein the plurality of wells in the middle filtration plate each include a side wall having an inner surface, and, located below the downstream surface of the filter, a bottom wall including a fluid flow port and a rib arrangement projecting upwardly from the bottom wall, the rib arrangement having a top surface spaced from the inner surface of the side wall, wherein the filter is sealed in the well by compression between an end of the downwardly projecting collar of the upper receiving plate and the top surface of the rib arrangement in the middle filtration plate; wherein the bottom wall of each of the plurality of wells in the middle filtration plate also includes a downwardly projecting collar surrounding the fluid flow port, wherein spaces between downwardly projecting collars of adjacent middle filtration plate wells form grooves with lower openings for receiving top ends of corresponding wells in the lower collection plate, wherein the fluid flow port in the middle filtration plate is arranged to allow a filtered fluid sample to pass from a well in the middle filtration plate to a corresponding well in the lower collection plate; and wherein side walls of wells at sidewalls of the middle filtration plate are receivable in corresponding grooves in the corresponding opposing sidewalls of the upper receiving plate; and, (c) the lower collection plate comprising a plurality of wells arranged to receive the filtered fluid sample passing through the fluid flow ports in the corresponding wells of the middle plate, the plurality of wells each having a top end and a bottom end, wherein the top end of each of the plurality of wells in the lower collection plate is receivable in a groove surrounding the downwardly projecting collar of a corresponding well in the middle filtration plate.

Methods of filtration using the embodiments of the multiwell device are also provided.

BRIEF DESCRIPTION OF THE SEVERAL VIEWS OF THE DRAWING(S)

Figure 1B:
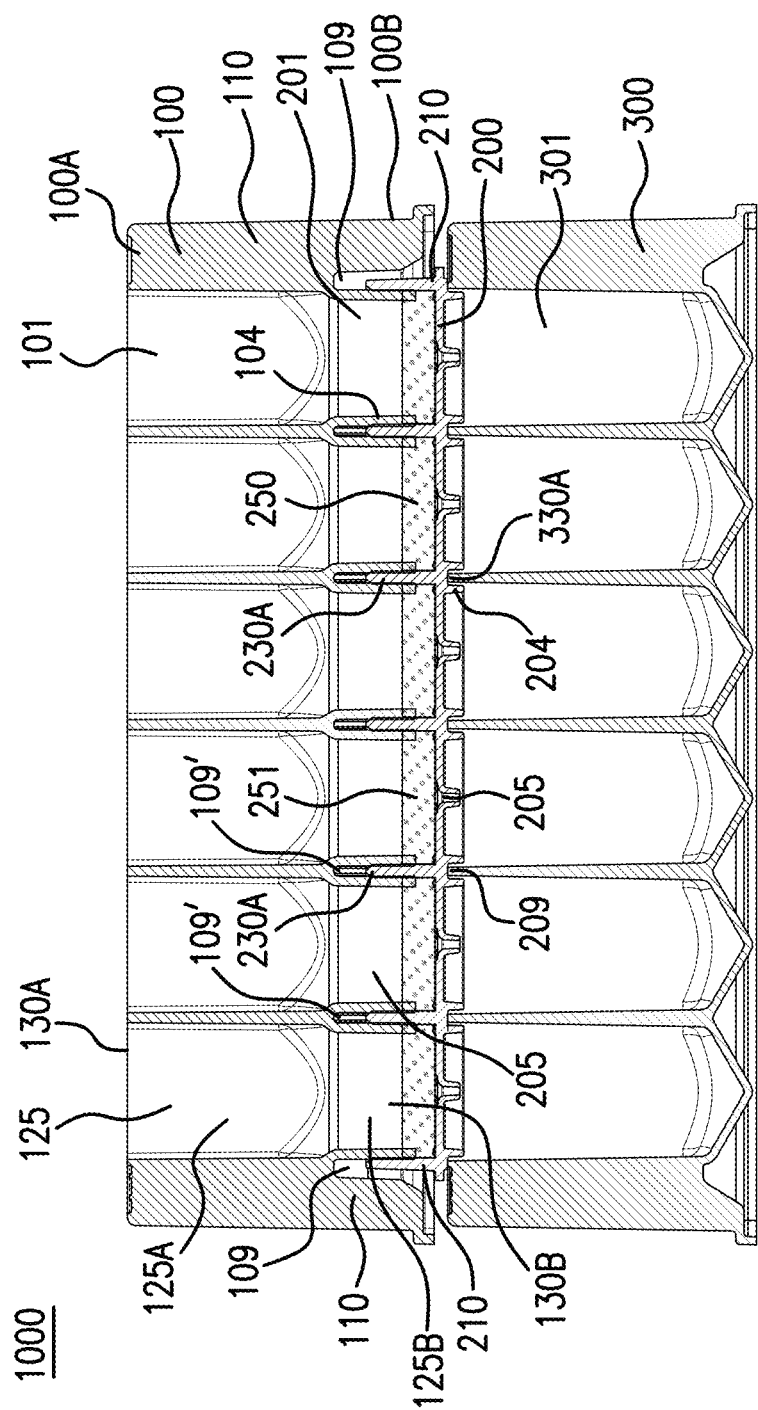
Figure 1C:
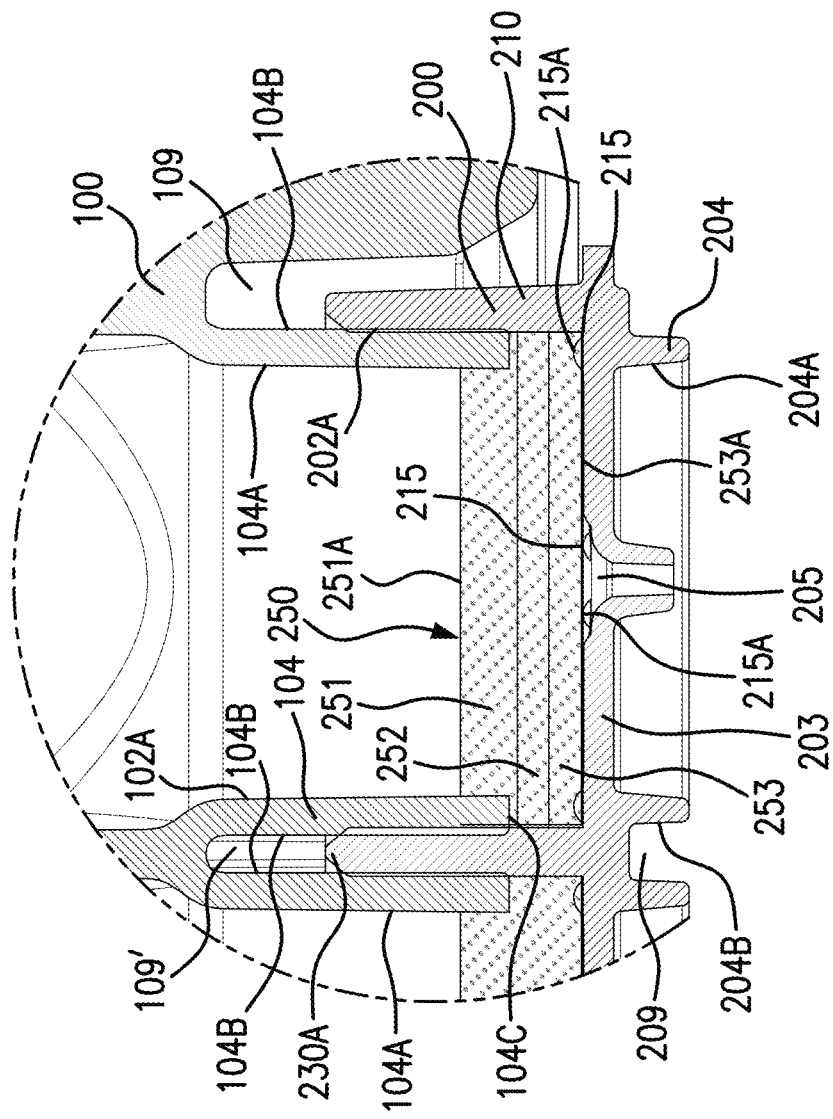

FIG. 1A is a top view of an assembled multiwell device according to an embodiment of the invention; FIG. 1B is a cross-sectional view of the assembled multiwell device along line A-A of FIG. 1B, showing an upper receiving plate, a middle filtration plate, and a lower collection plate; FIG. 1C is an enlarged sectional view showing a well in the filtration plate received in the bottom of a well in the upper receiving plate, also showing the filter sealed between the lower end of a collar in the upper receiving plate, and the upper surface of the rib arrangement in the middle filtration plate, wherein the end of the collar and the top surface of the rib arrangement compress the circumference of the filter.

Figure 2A:
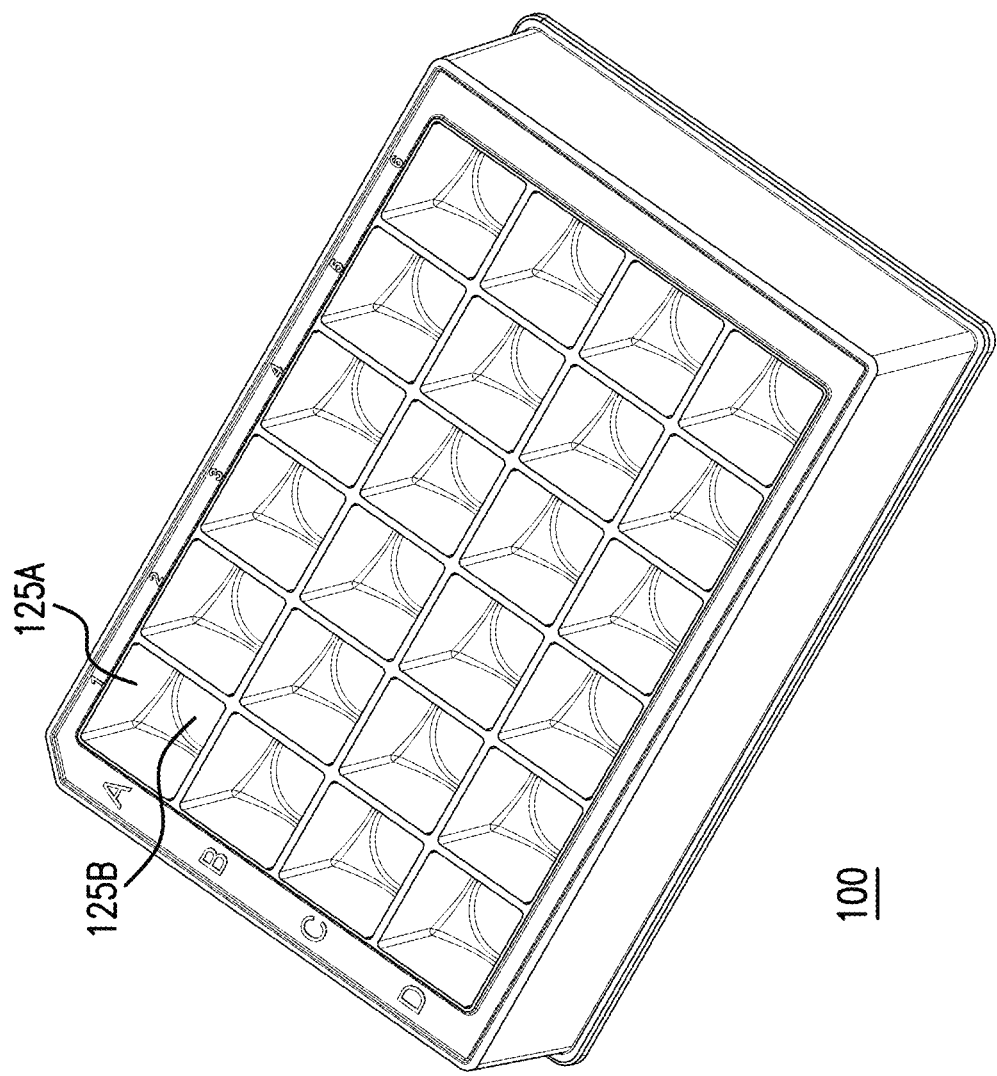
Figure 2B:
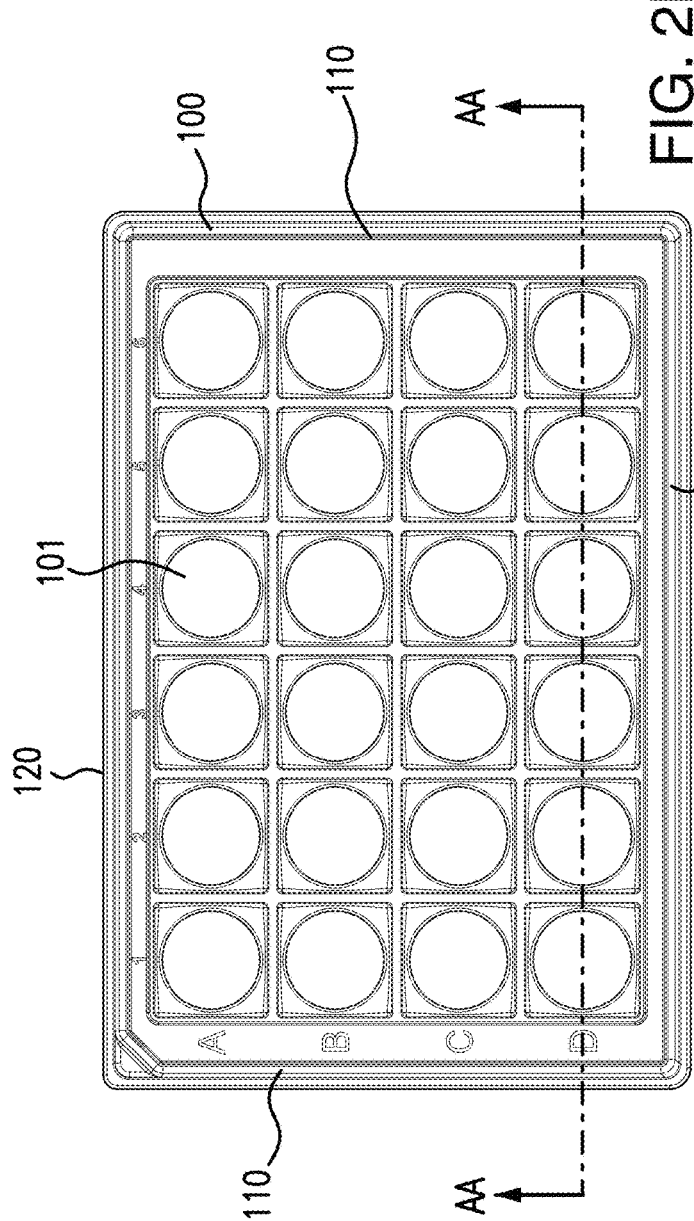
Figure 2D:
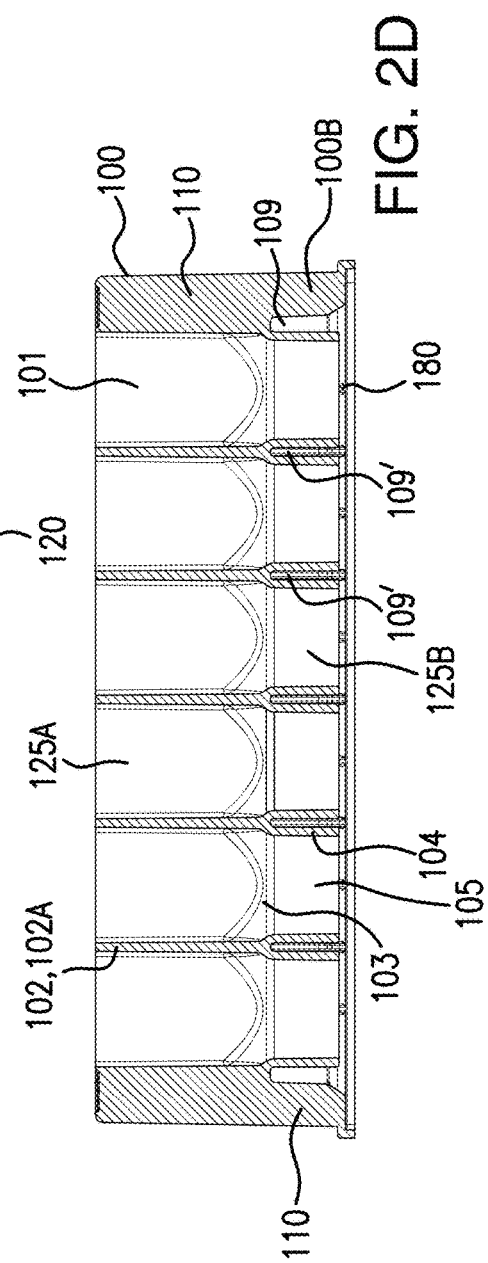
Figure 2C:
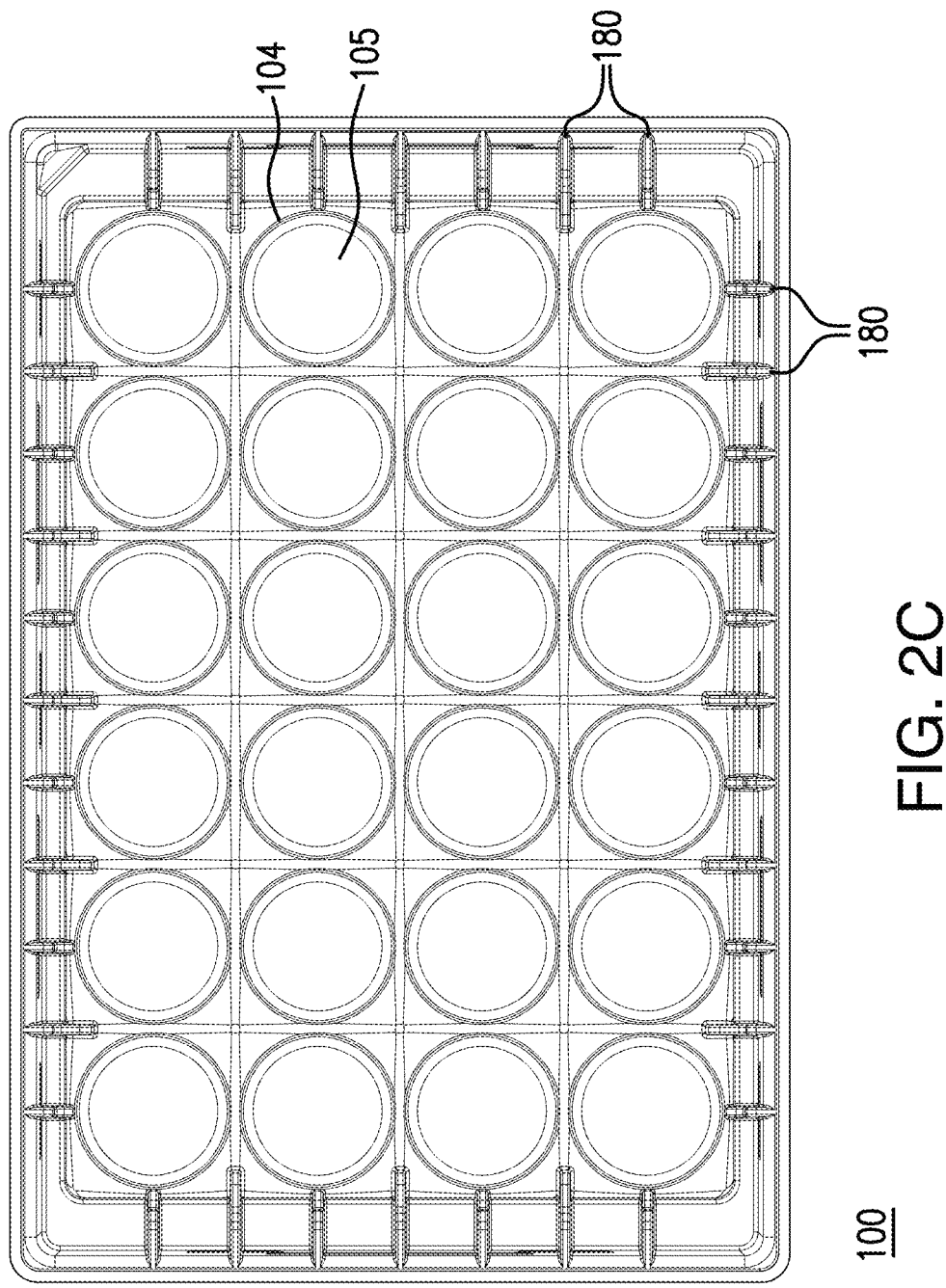

FIGS. 2A-2D show various views of the upper receiving plate. FIG. 2A shows a top perspective view, also showing the upper portions of the wells having a bore with a generally square shape; FIG. 2B shows a top view; FIG. 2C shows a bottom view also showing the lower portions of the wells having a bore with a generally annular shape; FIG. 2D shows a cross-sectional view along line AA-AA of FIG. 2B, also showing the inner surface of the side wall of each well and the downwardly sloped side wall of each well where the bore changes from a generally square shape to a generally annular shape, each well including a downwardly projecting collar providing a bottom fluid flow port, the collar having an inner surface and an outer surface, wherein the inner surface of the side wall is continuous with the inner surface of the collar, and space between the outer surfaces of adjacent collars forms a groove with a lower opening for receiving upper ends of the wells in the middle filtration plate, and the opposing side walls of the upper receiving plate each form a groove with a lower opening for receiving sidewalls of corresponding wells at corresponding side walls of the filtration plate.

Figure 3A:
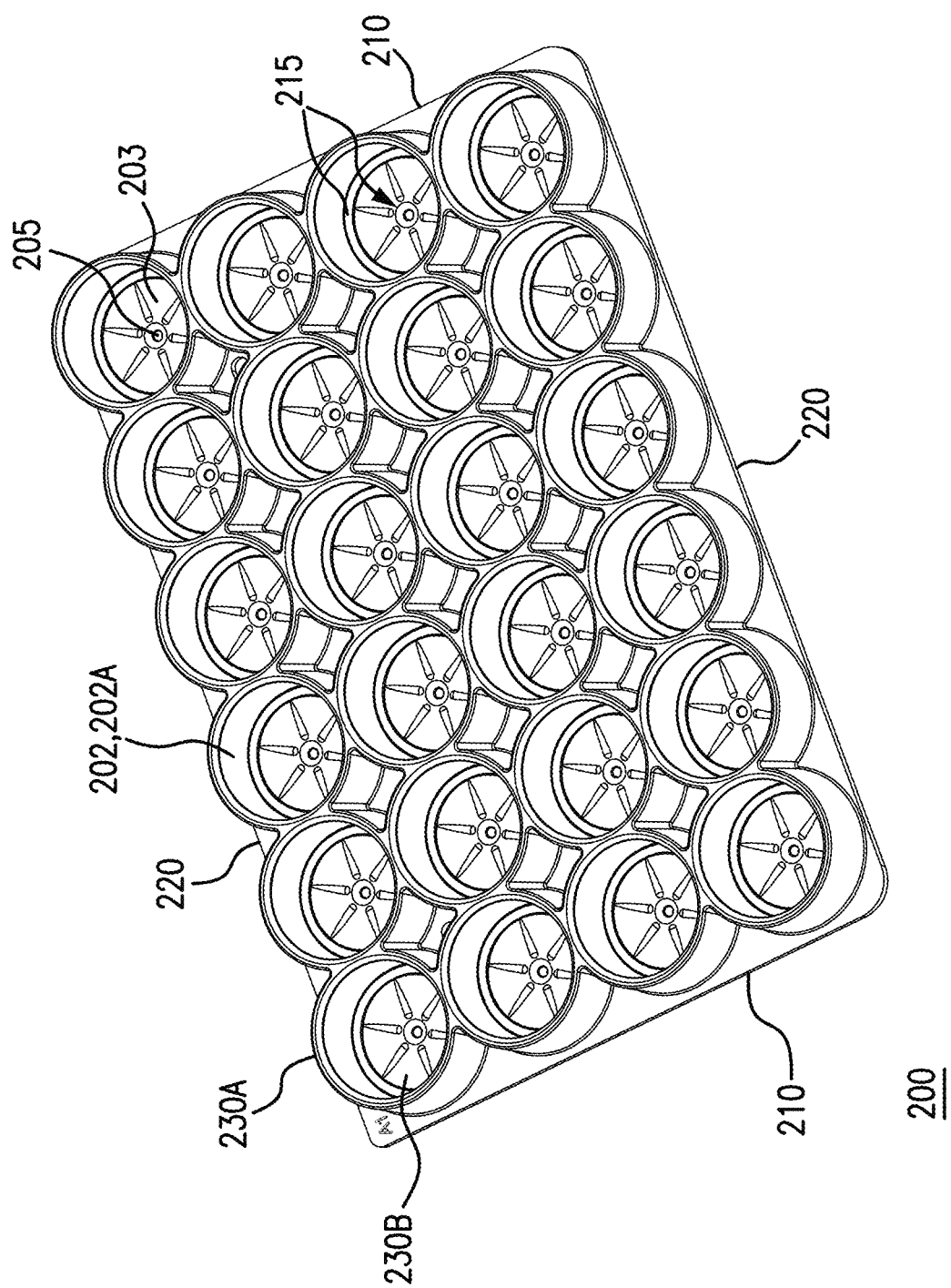
Figure 3B:
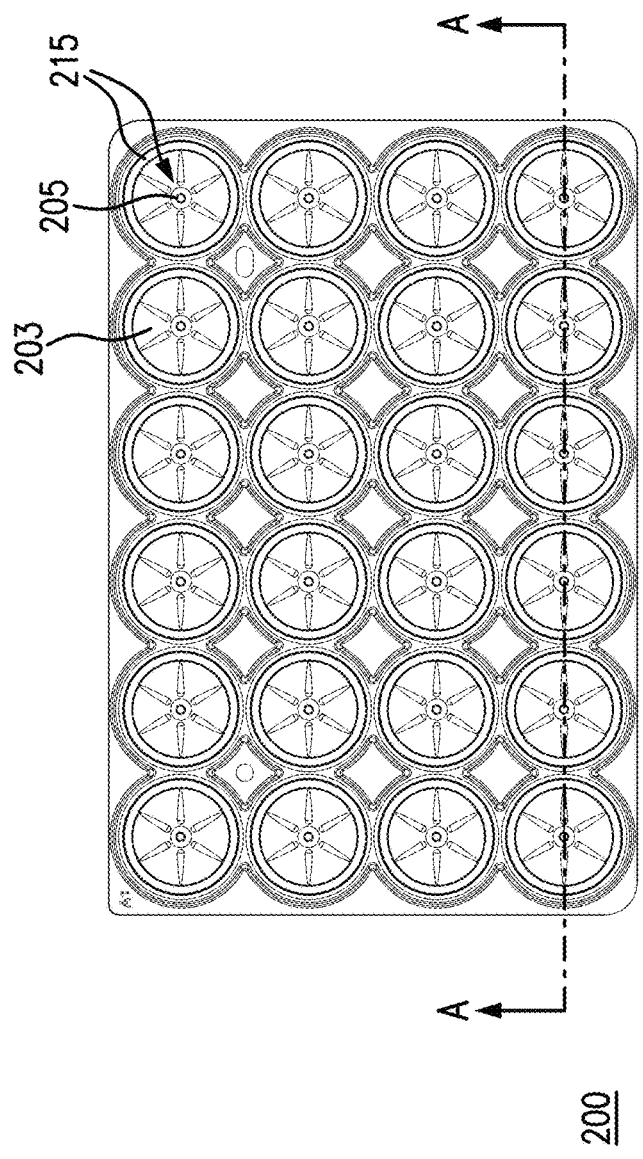
Figure 3D:
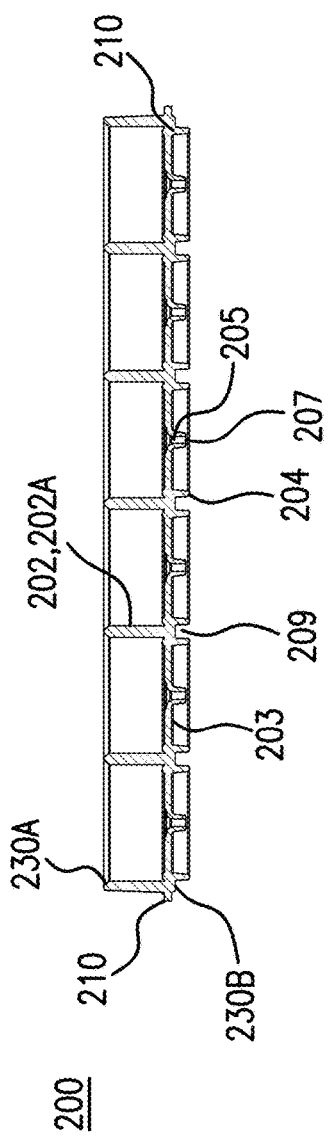
Figure 3C:
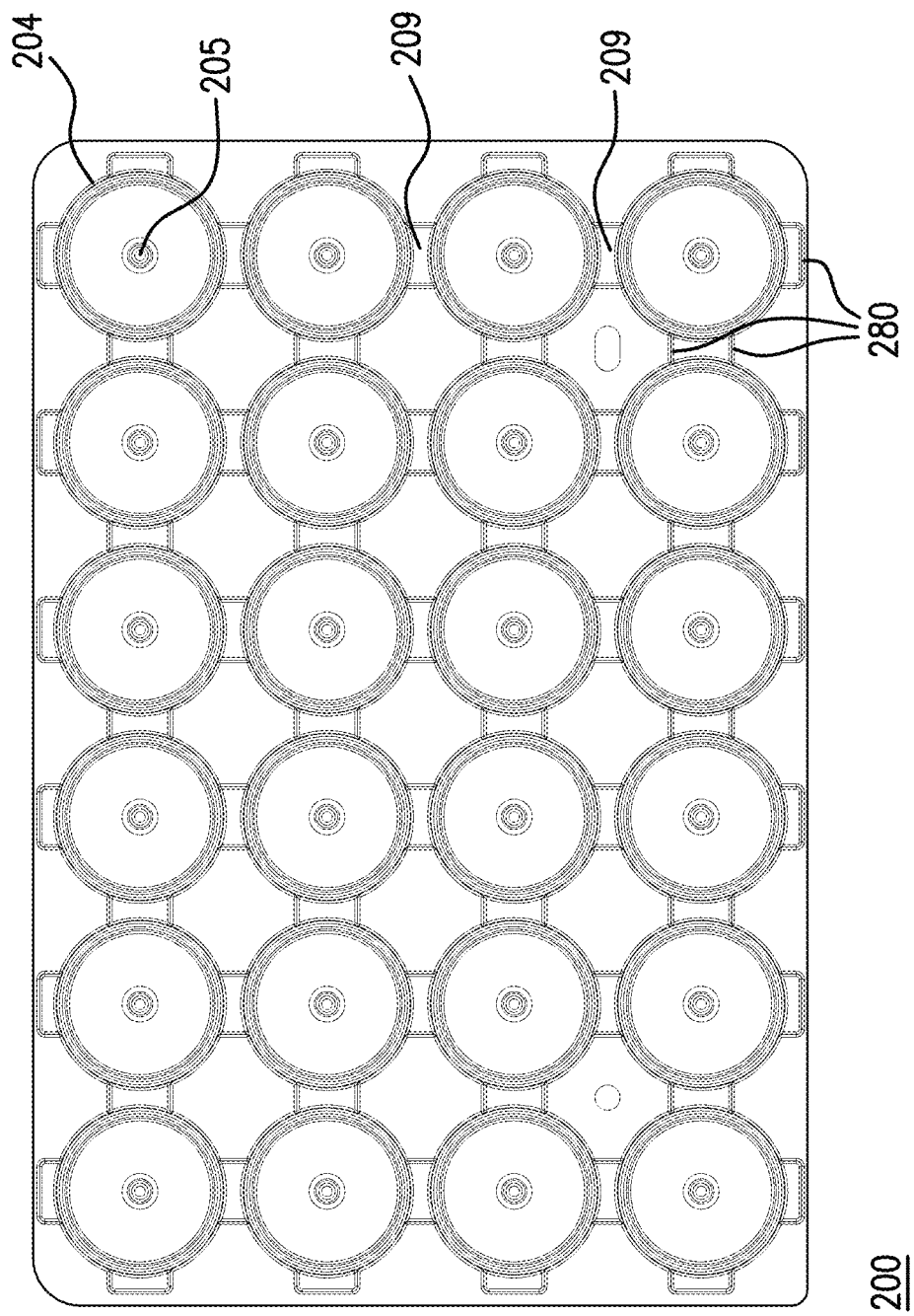
Figure 3E:
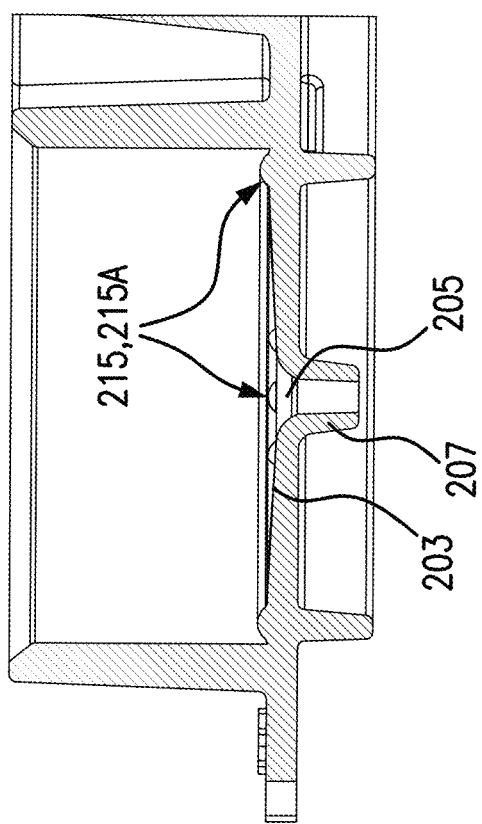
Figure 4B:
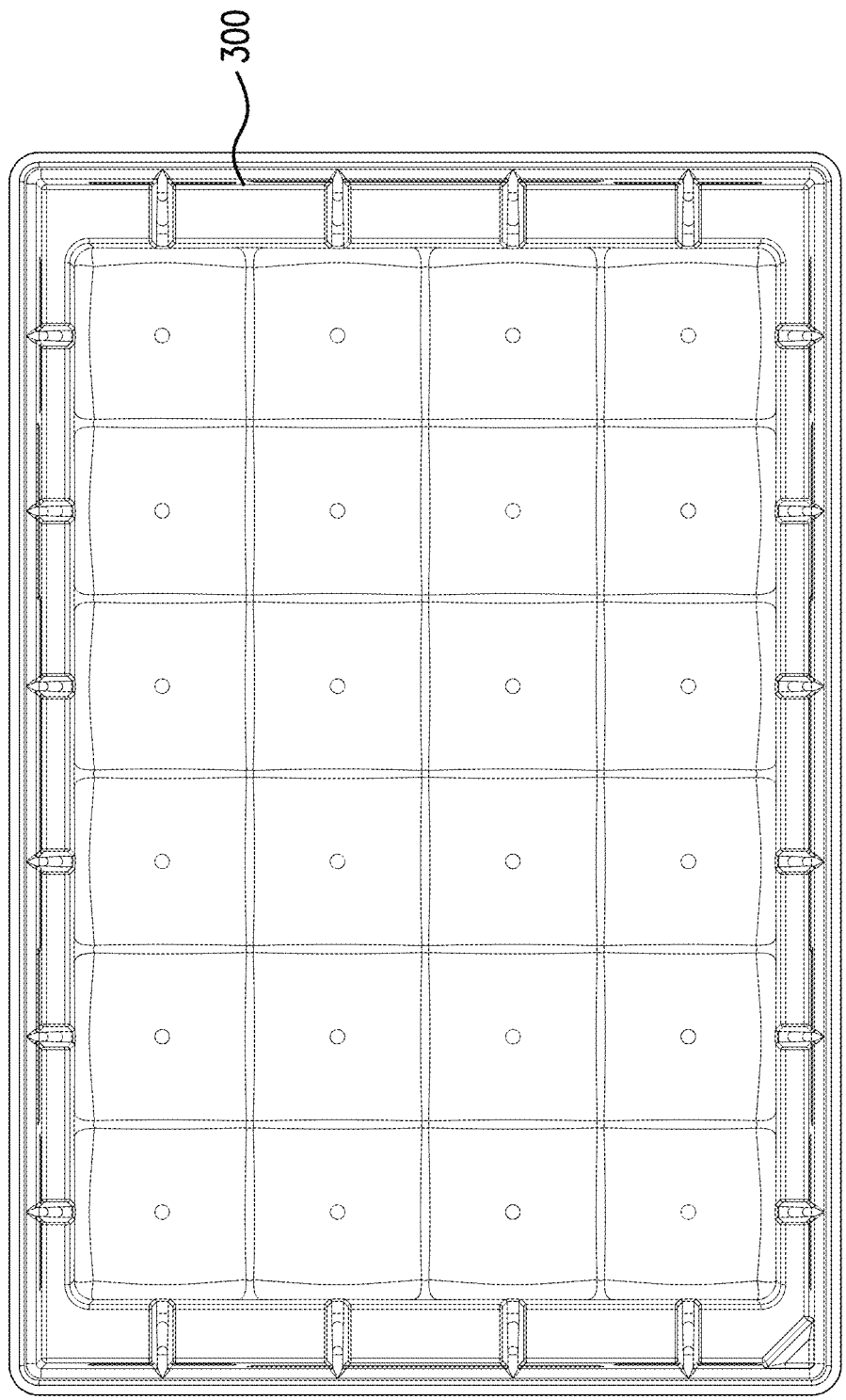

FIGS. 3A-3E show various views of the middle filtration plate without filters being present. FIG. 3A shows a top perspective view, also showing a fluid flow port and a rib arrangement having a radial configuration projecting upwardly from the bottom walls of middle filtration plate wells; FIG. 3B shows a top view; FIG. 3C shows a bottom view; FIG. 3D shows a cross-sectional view of the middle filtration plate along line A-A of FIG. 3A, showing collars downwardly projecting from the lower surface of the bottom wall of the middle filtration plate wells, and downwardly projecting spouts in fluid communication with each fluid flow port, wherein each collar is spaced away from the centrally located spout, and space between the outer surfaces of adjacent collars forms a groove with a lower opening for receiving upper ends of wells in the lower collection plate, and the upper ends of the wells are arranged to be received in the grooves between downwardly projecting collars in in corresponding wells in the upper receiving plate; FIG. 3E shows a cross-sectional view of a well along line B-B of FIG. 3A, showing the bottom wall having a rib arrangement having a top surface spaced from the inner surface of the side wall, the bottom wall being downwardly inclined toward the fluid flow port, and the downwardly facing spout communicating with the fluid flow port;

FIGS. 4A-4C show various views of the lower collection plate. FIG. 4A shows a top view; FIG. 4B shows a bottom view; FIG. 4C shows a cross-sectional view along line A-A of FIG. 4A, also showing the upper ends of the wells in the lower collection plate that fit in the corresponding grooves in the middle filtration plate.

Figure 5:
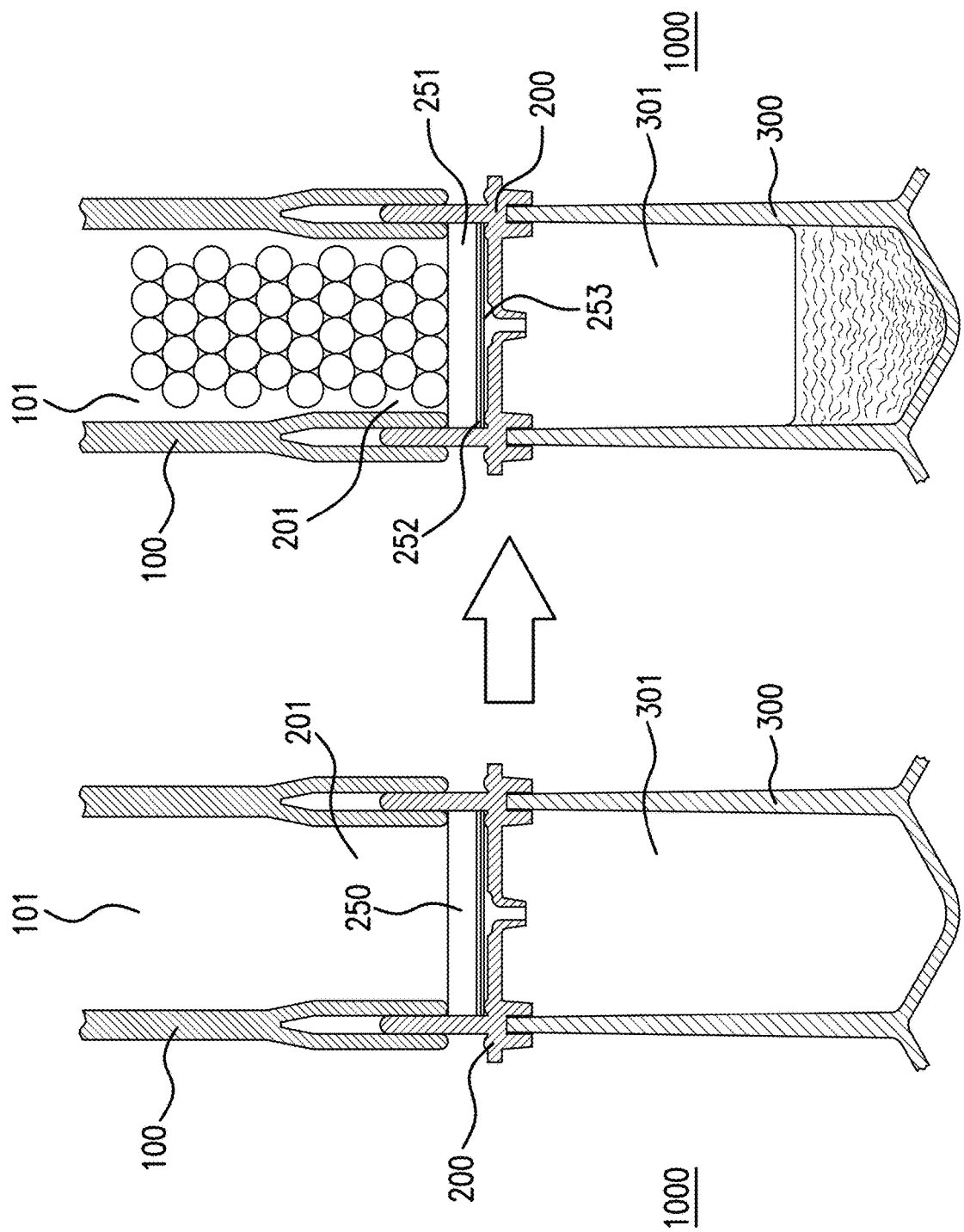

FIG. 5 is a diagrammatic cross-sectional view of wells in each of the three plates in an assembled device, showing (on the left) the wells before addition of a cell-containing fluid sample, and showing (on the right) a well with cells in the upper receiving plate, and a well with filtrate in the lower collection plate.

DETAILED DESCRIPTION OF THE INVENTION

In accordance with an embodiment of the invention, a multiwell device for processing fluid samples is provided, comprising: an upper receiving plate, a middle filtration plate, and a lower collection plate; (a) the upper receiving plate comprising a plurality of wells for receiving fluid samples comprising cells, the plurality of wells in the upper receiving plate each including a side wall having an inner surface, a bottom end including a downwardly projecting collar and a bottom fluid flow port, wherein the upper receiving plate includes two pairs of opposing sidewalls, and each opposing sidewall in at least one of the two pairs of opposing sidewalls in the upper receiving plate includes a groove having a lower opening for receiving side walls of corresponding wells at corresponding side walls on the middle filtration plate; (b) the middle filtration plate comprising a plurality of wells, the plurality of wells in the middle filtration plate each comprising a filter for filtering the fluid sample passing through the bottom fluid flow port of a corresponding well in the upper receiving plate; each filter comprising an upper depth filter layer having an average pore size in the range of from about 1 micrometer to about 20 micrometers, an upstream surface and an downstream surface, the upstream surface of the depth filter layer providing the upstream surface of the filter; a middle layer comprising a microporous membrane having an average pore size in the range of from about 0.4 micrometers to about 0.8 micrometers; and a bottom layer having an upstream surface and a downstream surface, comprising a microporous membrane having an average pore size of about 0.2 micrometers, the downstream surface of the microporous membrane having an average pore size of about 0.2 micrometers providing the downstream surface of the filter; wherein the plurality of wells in the middle filtration plate each include a side wall having an inner surface, and, located below the downstream surface of the filter, a bottom wall including a fluid flow port and a rib arrangement projecting upwardly from the bottom wall, the rib arrangement having a top surface spaced from the inner surface of the side wall, wherein the filter is sealed in the well by compression between an end of the downwardly projecting collar of the upper receiving plate and the top surface of the rib arrangement in the middle filtration plate; wherein the bottom wall of each of the plurality of wells in the middle filtration plate also includes a downwardly projecting collar surrounding the fluid flow port, wherein spaces between downwardly projecting collars of adjacent middle filtration plate wells form grooves with lower openings for receiving top ends of corresponding wells in the lower collection plate, wherein the fluid flow port in the middle filtration plate is arranged to allow a filtered fluid sample to pass from a well in the middle filtration plate to a corresponding well in the lower collection plate; and wherein side walls of wells at sidewalls of the middle filtration plate are receivable in corresponding grooves in the corresponding opposing sidewalls of the upper receiving plate; and, (c) the lower collection plate comprising a plurality of wells arranged to receive the filtered fluid sample passing through the fluid flow ports in the corresponding wells of the middle plate, the plurality of wells each having a top end and a bottom end, wherein the top end of each of the plurality of wells in the lower collection plate is receivable in a groove surrounding the downwardly projecting collar of a corresponding well in the middle filtration plate.

Preferably, the downwardly projecting collars in the upper receiving plate each have an inner surface and an outer surface, and space between the outer surfaces of adjacent downwardly projecting collars in the upper receiving plate form grooves with lower openings for receiving tapered top ends of corresponding wells in the middle filtration plate.

Methods of filtration using the embodiments of the multiwell device are also provided.

In one embodiment, a method for obtaining proteins from a cell-containing fluid is provided, the method comprising: placing samples of cell-containing fluid in wells of the upper receiving plate of an embodiment of the multiwell device; filtering the samples; and, obtaining protein-containing fluid in wells in the lower collection plate.

Advantageously, proteins can be obtained in a less labor intensive manner, and in less time. Additionally, the use of a multiwall device instead of multiple centrifuge tubes, pipette tips, sterile filters, and syringes, is more environmentally friendly. Moreover the use of an upper receiving plate having an upper square-shaped or generally square-shaped bore, and a lower annularly-shaped or generally annularly-shaped bore, allows filtration of a larger volume of sample while still sealing the filter in a well.

Each plate (which is typically generally rectangularly arranged) includes a plurality of wells, in the illustrated embodiment, 24 wells, though plates can include a greater number of wells, e.g., 94 wells, or 384 wells, or a greater number than 384 wells, or fewer than 24 wells. Typically, the wells are arranged in a two-dimensional configuration. With the exception of the upper portions of the wells in the upper receiving plate, the wells are typically cylindrical, and the wells have fluid-impermeable walls, and have a depth and width for the desired use and amount of fluid to be sampled.

Each of the wells in the filtration plate includes a filter comprising three layers or three filter elements, in some embodiments, the filter consists of three layers or three filter elements. The filter is positioned at the bottom of the well. As will be described in more detail below, the upper receiving plate and the filtration plate include structures contacting portions of the respective top and bottom surfaces of the filter, such that the filter is sealed in the well without fluid bypassing.

Each of the components of the invention will now be described in more detail below, wherein like components have like reference numbers.

In accordance with the illustrated embodiment shown particularly in FIGS. 1B and 5, a multiwell device 1000 comprises an upper receiving plate 100 including a plurality of wells 101; a middle filtration plate 200 including a plurality of wells 201, each well including a filter 250; and a lower collection plate 300 including a plurality of wells 301.

The illustrated embodiment of the upper receiving plate 100 is shown in more detail in FIGS. 1A-1C, 2A-2D. The illustrated upper receiving plate has an upper portion 100A and a lower portion 100B, two pairs of opposing side walls 110 and 120, and a plurality of wells 101 for receiving fluid samples including cells. The wells 101 have side walls 102, having inner surfaces 102A, a top end 130A, a bottom end 130B, a bottom wall 103, a downwardly projecting collar 104 having a receiving plate bottom fluid flow port 105. The wells each have a bore 125. The downwardly projecting collar 104 has an inner surface 104A that is continuous with inner surface 102A, an outer surface 104B, and an end 104C (see, FIG. 1C). As will be discussed in more detail below, the collar end 104C compresses the upper surface of the filter in the well of the middle filtration plate, to assist in sealing the filter in the well.

Preferably, space between the outer surfaces 104B of adjacent downwardly projecting collars 104 in the receiving plate form grooves 109' with lower openings for receiving top ends 230A of corresponding wells 201 in the middle filtration plate 200 (see, FIGS. 1B and 1C). Using FIG. 1C for reference, preferably, the top ends 230A that are received in grooves 109' are tapered, and in some embodiments, the lower portions of outer surfaces 104B are indented, and the tapered top ends of 230 push the adjacent outer surfaces apart and reach beyond the indents when being received in the upper receiving plate.

Preferably, as particularly shown in FIG. 2A, the upper bore 125A of the wells has a square configuration, and the lower bore 125B has an annular configuration.

At least one pair of opposing side walls (illustrated as opposing side walls 110) includes, at the lower portion 100B, a groove 109 with a lower opening for receiving side walls 202 of corresponding wells at corresponding side walls 210 on the middle filtration plate 200 (see, FIGS. 1B and 1C).

As shown in FIGS. 2C and 2D, the lower portion of the receiving plate can include a plurality of strengthening ribs 180.

The illustrated embodiment of the middle filtration plate 200 is shown in more detail in FIGS. 1B, 1C, and 3A-3E. The illustrated middle filtration plate includes two pairs of opposing side walls 210 and 220, and a plurality of wells 201 for receiving fluid samples containing cells passing from upper receiving plate wells 101. The wells 201 have side walls 202, having inner surfaces 202A, a top end 230A (that is tapered for those ends fitting in groove 109' as shown in FIG. 1C), a bottom end 230B, a bottom wall 203 having a rib arrangement 215 projecting upwardly from the bottom wall, the rib arrangement having top surfaces 215A spaced from the inner surface of the side wall (see, FIGS. 1C and 3E), a filtration plate fluid flow port 205 communicating with a spout 207, and a downwardly projecting collar 204 surrounding, and spaced away from the spout, the collar having an inner surface 204A and an outer surface 204B. FIG. 3E shows the bottom wall downwardly inclined toward the fluid flow port. Spaces between outer surfaces of downwardly projecting collars of adjacent middle filtration plate wells form grooves 209 with lower openings for receiving top ends 330A of corresponding wells 301 in the lower collection plate 300 (see, FIG. 1B).

The illustrated rib arrangement 215 has an annular upwardly projecting outer rib near the side walls and, more centrally located, a plurality of radially arranged upwardly projecting ribs. Preferably, as illustrated, the upper surfaces of the ribs are non-planar, e.g., rounded. The plurality of radially arranged upwardly projecting ribs can provide a drainage grid for the well.

As shown in FIG. 3C, the lower portion of the middle filtration plate can include a plurality of strengthening ribs 280.

As shown in FIGS. 1B, and 1C, the wells 201 of the middle filtration plate 200 include filters 250, each comprising an upper layer comprising a depth filter 251, a middle layer comprising a microporous membrane 252, and a bottom layer comprising a microporous membrane 253. Each layer has an upstream surface and a downstream surface, wherein the upstream surface of the upper layer comprises the upstream surface 251A of the filter and the downstream surface of the bottom layer comprises the downstream surface 253A of the filter.

As illustrated in FIG. 1C, the collar end 104C of the upper receiving plate 100 compresses the upstream surface of the filter in the well of the middle filtration plate, and the upper surface 215A of the rib arrangement 215 (particularly the upper surface of the annular outer rib near the side wall) compresses the downstream surface of the filter, thus sealing the filter in the well without allowing bypassing.

A filter layer can have any suitable pore structure, e.g., a pore size (for example, as evidenced by bubble point, or by $K_L$ as described in, for example, U.S. Pat. No. 4,340,479, or evidenced by capillary condensation flow porometry), a pore rating, a pore diameter (e.g., when characterized using the modified OSU F2 test as described in, for example, U.S. Pat. No. 4,925,572), or removal rating that reduces or allows the passage therethrough of one or more materials of interest as the fluid is passed through the layer.

Typically, the depth filter layer has an average pore size in the range of from about 1 micrometer to about 20 micrometers, preferably in the range of from about 6 micrometers to about 15 micrometers. Typically, the middle layer membrane an average pore size in the range of from about 0.4 micrometers to about 0.8 micrometers, and in some embodiments, it has an average pore size of about 0.65 micrometers. The bottom layer membrane is preferably rated for providing sterile filtration, e.g., having an average pore rating of about 0.2 micrometers.

A variety of suitable filter layers are commercially available.

The filter layers can have any desired critical wetting surface tension (CWST, as defined in, for example, U.S. Pat. No. 4,925,572). The CWST can be selected as is known in the art, e.g., as additionally disclosed in, for example, U.S. Pat. Nos. 5,152,905, 5,443,743, 5,472,621, and 6,074,869.

The illustrated embodiment of the lower collection plate 300 is shown in more detail in FIGS. 1B, and 4A-4C. The illustrated lower collection plate includes two pairs of opposing side walls 310 and 320, and a plurality of wells 301 for receiving filtered fluid samples passing from middle filtration plate wells 201. The wells 301 have side walls 302, having inner surfaces 302A, a top end 330A, a bottom end 330B, a bottom wall 303. As shown in FIG. 1B, the top ends 330A of wells in the lower collection plate 300 are receivable in grooves 209 surrounding the downwardly projecting collars 204 of corresponding wells 201 in the middle filtration plate 200.

The plates can be fabricated from any suitable rigid impervious material, including any impervious thermoplastic material, which is compatible with the fluid being processed. For example, the plates can be fabricated from a metal, such as stainless steel, or from a polymer. In a preferred embodiment, the plates are fabricated from a polymer, such as an acrylic, polypropylene, polystyrene, or a polycarbonated resin.

The following example further illustrates the invention but, of course, should not be construed as in any way limiting its scope.

EXAMPLE

This example demonstrates the separation of proteins from a mammalian (Chinese Hamster Ovary; (CHO)) cell-containing sample of fluid. The samples are 5 ml CHO cell cultures with a density of ≥25 million cells/ml, spiked with gamma globulin (containing IgG) to have a higher quantity of proteins to assess (total proteins about 10 mg and IgG about 3 mg).

Multiwell devices are assembled as generally shown in the Figures. The filter contains three layers. The most upstream layer is a depth filter sheet (SEITZ K Cellulose 700P; Pall Corporation; Port Washington, N.Y.), the middle layer is a 0.65 µm asymmetric polyethersulphone membrane and the bottom layer is a 0.2 µm symmetric polyethersulphone membrane (the middle layer combined with the bottom layer is commercially available as the SUPOR EKV filter; Pall Corporation; Port Washington, N.Y.).

One set of samples is filtered using a vacuum manifold apparatus (Pall Corporation Multi-Well Plate Vacuum Manifold), another set of cells is filtered using centrifugation (Eppendorf 5810 centrifuge).

The results are as follows:

| 5 ml sample concentrated CHO cell sample | Upstream | Downstream filtrate (15 in Hg vacuum) | Downstream filtrate (1,000 × g centrifugation) |
|---|---|---|---|
| Time for passage through filter (min.) | — | 20.2 ± 6.3 | 15 |
| Hold-up volume (µL) | | 300-450 | 400-450 |
| pH | 7.2 | 7.3 | 6.8 |
| Conductivity (µS/cm) | Approx. 10,100 | Approx. 9,200 | Approx. 9,800 |
| Turbidity (NTU) | Approx. 1,900-2,600 | Approx. 1.8 | Approx. 2.4 |
| Optical Density at 600 nm | Approx. 18-19 | 0 | 0 |
| Total protein recovery (%) | | 98.3 ± 8.2 (78 wells from 14 plates) | 95.4 ± 11.4 (79 wells from 14 plates) |
| IG protein recovery (%) | | 91.3 ± 11 (77 wells from 14 plates) | 85.0 ± 6.9 (34 wells from 14 plates) |

The results are generally similar for filtration using both vacuum and centrifugation.

This Example showed that the device removes cells influencing absorbency and turbidity and provides for the recovery of proteins.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A multiwell device for processing fluid samples comprising:
   an upper receiving plate, a middle filtration plate, and a lower collection plate;
   (a) the upper receiving plate comprising a plurality of wells for receiving fluid samples comprising cells, the plurality of wells in the upper receiving plate each including a side wall having an inner surface, a bottom end including a downwardly projecting collar and a bottom fluid flow port, wherein the upper receiving plate includes two pairs of opposing sidewalls, and each opposing sidewall in at least one of the two pairs of opposing sidewalls in the upper receiving plate includes a groove having a lower opening for receiving side walls of corresponding wells at corresponding side walls on the middle filtration plate;

(b) the middle filtration plate comprising a plurality of wells, the plurality of wells in the middle filtration plate each comprising a filter for filtering the fluid sample passing through the bottom fluid flow port of a corresponding well in the upper receiving plate;

each filter comprising an upper depth filter layer having an average pore size in the range of from about 1 micrometer to about 20 micrometers, an upstream surface and an downstream surface, the upstream surface of the upper depth filter layer providing the upstream surface of the filter; a middle layer comprising a microporous membrane having an average pore size in the range of from about 0.4 micrometers to about 0.8 micrometers; and a bottom layer having an upstream surface and a downstream surface, comprising a microporous membrane having an average pore size of about 0.2 micrometers, the downstream surface of the microporous membrane having an average pore size of about 0.2 micrometers providing the downstream surface of the filter;

wherein the plurality of wells in the middle filtration plate each include a side wall having an inner surface, and, located below the downstream surface of the filter, a bottom wall including a fluid flow port and a rib arrangement projecting upwardly from the bottom wall, the rib arrangement having a top surface spaced from the inner surface of the side wall, wherein the filter is sealed in the well by compression between an end of the downwardly projecting collar of the upper receiving plate and the top surface of the rib arrangement in the middle filtration plate;

wherein the bottom wall of each of the plurality of wells in the middle filtration plate also includes a downwardly projecting collar surrounding the fluid flow port, wherein spaces between downwardly projecting collars of adjacent middle filtration plate wells form grooves with lower openings for receiving top ends of corresponding wells in the lower collection plate, wherein the fluid flow port in the middle filtration plate is arranged to allow a filtered fluid sample to pass from a well in the middle filtration plate to a corresponding well in the lower collection plate; and wherein side walls of wells at sidewalls of the middle filtration plate are receivable in corresponding grooves in the corresponding opposing sidewalls of the upper receiving plate;

and, (c) the lower collection plate comprising a plurality of wells arranged to receive the filtered fluid sample passing through the fluid flow ports in the corresponding wells of the middle plate, the plurality of wells in the lower collection plate each having a top end and a bottom end, wherein the top end of each of the plurality of wells in the lower collection plate is receivable in a groove surrounding the downwardly projecting collar of a corresponding well in the middle filtration plate.

2. The multiwell device of claim 1, wherein the downwardly projecting collars in the upper receiving plate each have an inner surface and an outer surface, and space between the outer surfaces of adjacent downwardly projecting collars in the upper receiving plate form grooves with lower openings for receiving tapered top ends of corresponding wells in the middle filtration plate.

3. A method for obtaining proteins from a cell-containing fluid, the method comprising:
placing samples of cell-containing fluid in wells of the upper receiving plate of the multiwell device of claim 2;
filtering the samples; and,
obtaining protein-containing fluid in wells in the lower collection plate.

4. The multiwell device of claim 2, wherein lower portions of the outer surfaces of the adjacent downwardly projecting collars in the upper receiving plate are indented, and the tapered top ends of the corresponding wells in the middle filtration plate push the adjacent outer surfaces apart and reach beyond the indented lower portions when being received in the upper receiving plate.

5. A method for obtaining proteins from a cell-containing fluid, the method comprising:
placing samples of cell-containing fluid in wells of the upper receiving plate of the multiwell device of claim 1;
filtering the samples; and,
obtaining protein-containing fluid in wells in the lower collection plate.

* * * * *